(12) United States Patent
Pastyr et al.

(10) Patent No.: US 6,259,762 B1
(45) Date of Patent: Jul. 10, 2001

(54) RADIATION SYSTEM WITH SEVERAL RADIATION SOURCES DIRECTED TO A CONTROL POINT

(75) Inventors: Otto Pastyr, Leimen; Wolfgang Schlegel, Heidelberg; Simone Barthold, Eppelheim; Karl-Heinz Höver, Sinsheim; Gernot Echner, Wiesenbach, all of (DE)

(73) Assignee: Deutsches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 0 days.

(21) Appl. No.: 09/486,193
(22) PCT Filed: Aug. 19, 1998
(86) PCT No.: PCT/DE98/02491
  § 371 Date: Aug. 23, 2000
  § 102(e) Date: Aug. 23, 2000
(87) PCT Pub. No.: WO99/08750
  PCT Pub. Date: Feb. 25, 1999

(30) Foreign Application Priority Data
Aug. 20, 1997 (DE) .............................. 197 36 192

(51) Int. Cl.⁷ .................................................. H01J 35/06
(52) U.S. Cl. .............................................. 378/65; 378/64
(58) Field of Search ............................... 378/65, 55, 64, 378/21

(56) References Cited

U.S. PATENT DOCUMENTS

| 3,670,163 | * | 6/1972 | Lajus ....................................... 250/50 |
| 3,720,817 | | 3/1973 | Dinwiddie ........................ 235/151.11 |
| 4,230,129 | | 10/1980 | LeVeen ................................. 128/804 |
| 4,233,519 | * | 11/1980 | Coad ..................................... 250/514 |
| 5,337,231 | * | 8/1994 | Nowak et al. ................... 364/413.24 |
| 5,448,611 | | 9/1995 | Kerjean .................................. 378/65 |
| 5,537,452 | | 7/1996 | Shepherd et al. ....................... 378/65 |
| 5,627,870 | | 5/1997 | Kopecky ................................ 378/65 |
| 5,869,841 | * | 2/1999 | Smither .............................. 250/505.1 |

FOREIGN PATENT DOCUMENTS

| 1 464 657 | 12/1968 | (DE) . |
| 30 00 439 A1 | 7/1981 | (DE) ................................ G12K/1/08 |
| 0 034735 A3 | 2/1981 | (EP) .................................. A61F/7/00 |
| 0 655 262 A1 | 4/1994 | (EP) .................................. A61N/5/10 |
| 1121582 | 7/1968 | (GB) . |

* cited by examiner

Primary Examiner—Robert H. Kim
Assistant Examiner—Irakli Kiknadze
(74) Attorney, Agent, or Firm—Steven J. Hultquist; Marianne Fuierer

(57) ABSTRACT

The radiation system has several radiation sources aimed toward a central point. These radiation sources are on arc element that pivots on an axis. The center can hence be irradiated from different sides. The radiation sources preferably have irregularly adjustable diaphragms. The system is suitable for irradiating any part of the human body. It is easy to manufacture and simple to used.

13 Claims, 2 Drawing Sheets

RADIATION SYSTEM WITH SEVERAL RADIATION SOURCES DIRECTED TO A CONTROL POINT

Figure 1:
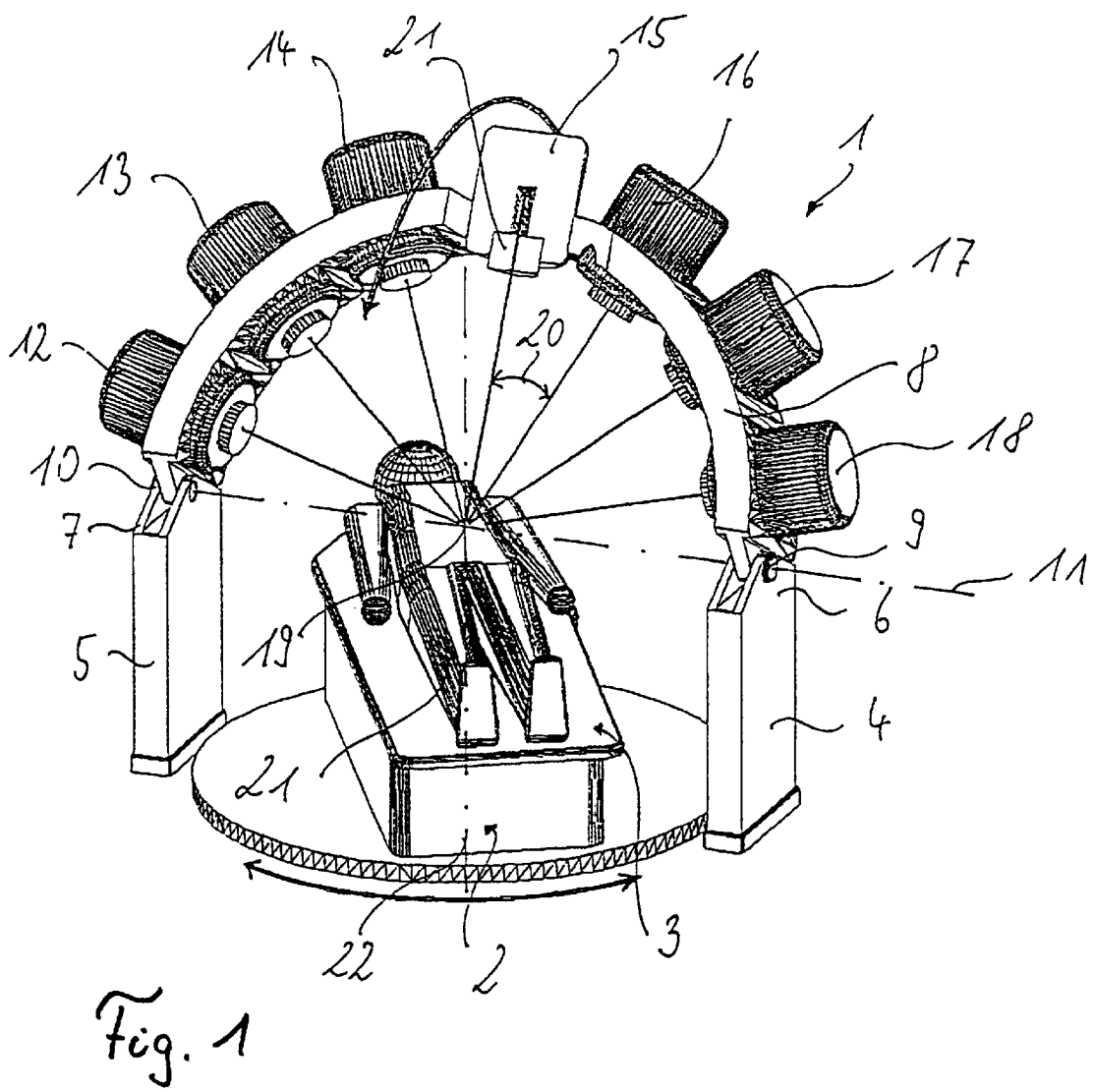

The invention concerns a radiation system with several radiation sources aimed at a central point. Such a radiation system is known by the name of a "gamma knife". This system is a radioisotope irradiation system with 201 cobalt sources. These cobalt sources are on the lateral surface of a hollow sphere an all point toward a center. This system is highly suitable for irradiating the human head positioned inside the hollow sphere. This device cannot be used to irradiate the rest of the body, however. In addition, the gamma knife is relatively expensive to manufacture, and servicing an operation are costly and time-consuming. Only a limited degree of fractionated irradiation can be done with the gamma knife.

Stereotactic linear accelerators represent another prior-art irradiation system. These systems must be carefully adjusted before use in radiosurgery, and the adjustment must be continuously monitored. The resulting involved quality assurance makes it difficult to use the system in small institutions and hospitals. In addition, the operation and service costs are high for linear accelerators. Furthermore, the radiation time is relatively long due to the sequential processing of the individual radiation fields.

The invention is based on the problem of offering an irradiation system that can be used for the entire body.

This problem is solved by placing the radiation source on an arc element that pivots on a first axis, and the arc element and a patient table rotate relative to each other on a second axis perpendicular to the first axis.

The use of a pivotable arc element allows a point or area to be irradiated from several sides using fewer radiation sources. In addition, the selected distance of the radiation sources to the human body can be such that the body is placed under the arch or in the arc. Since only one arc element has to be moved on a fixed axis, a high degree of mechanical precision can be attained using simple means.

The device according to the invention provides that all radiation sources are directed toward a central point. The arc is also able to rotate relative to the patient table on an axis perpendicular to the swivel axis of the arc. This makes it possible to irradiate the central point from different sides with a radiator and radiate the center from radically different angles with the same or different radiators while moving the device on the two described axes.

The entire system can be easily constructed, and its easy operation allows it to be used in less developed countries.

It is advantageous when the arc element describes an arc of less than ca 270° and preferably ca 180°. There remains enough room under the arc element to securely place a patient table.

It is particularly advantageous when the axis on which the arc element pivots runs through the central point at which the radiation sources are aimed. This allows a point to be irradiated from several sides when the arc element is pivoted.

In one advantageous embodiment of the radiation system, the axis is a hollow shaft. Since this allows a view through the shaft, it is easier to position the irradiated body under the arc element. If the positioning is automatic, a laser or other measuring devices or an imaging system can be located in the hollow shaft.

It is advantageous when each radiation source has a diaphragm. Depending on the use, the diaphragms can be adjusted the same or differently from radiation source to radiation source.

A particularly advantageous diaphragm can be irregularly adjusted since such a diaphragm can be optimally adapted to the area to be irradiated. The setting of the diaphragm can also be varied while the arc element is moved so that a different diaphragm setting can selected depending on the direction of the radiation.

To securely position the patient, it is suggested that the radiation system have a table that can be positioned relative to the arc element. Such a table is preferably adjustable in the x, y and z axes so that the center of the radiation sources can be aligned with the body part to be irradiated by moving the table while the arc element remains stationary.

The table can be advantageously rotated around an axis that intersects the center and is perpendicular to the surface on which the patient rests. If the table e.g. is rotatable on a y-axis, the arc element can be swung on any axis lying in the x-z plane. In addition, rotating the human body on the y-axis allows the central point at which the radiation sources are aimed to be irradiated from different sides.

A simple radiation system design has 5–10 radiators. This corresponds to an angle between the radiators of 20°–30° if the radiators are on a semicircular arc element. The use of fewer radiators lowers the cost of each radiation source.

Given the relatively high costs of individual radiation sources and diaphragms, it can be advantageous when at least one radiation source is moveably mounted on the arc element. All radiation sources may be mounted on the arc element so that they can shift a certain angle.

To easily irradiate a human body, it is suggested that the angle between the radiation sources and the center be ca 1 m. The arc then has an opening of ca 2 m in which the patient can be placed.

In one advantageous embodiment of the radiation source, the radiators are designed as containers that allow the radiation source to be moved. The radiation sources therefore do not have to be changed locally. It is very dangerous for the operating personnel to change conventional radiators, and it is expensive since only specialists can change them. The radiators according to the invention designed as containers can e.g. be screwed via a thread into the arc element and can be screwed out of the arc element and exchanged after the radiation source fails. The used radiators are returned to the radiator manufacturer together with the containers, and a new radiator container is screwed into the arc in place of the original radiation container. They are therefore exchanged quickly and safely, and this can be done in less developed nations as well.

The design of the radiators as transportable containers can also be used for other radiation devices independent of the described radiation system.

A preferred exemplary embodiment of the invention is shown in the drawing and will be explained in the following.

Figure 2:
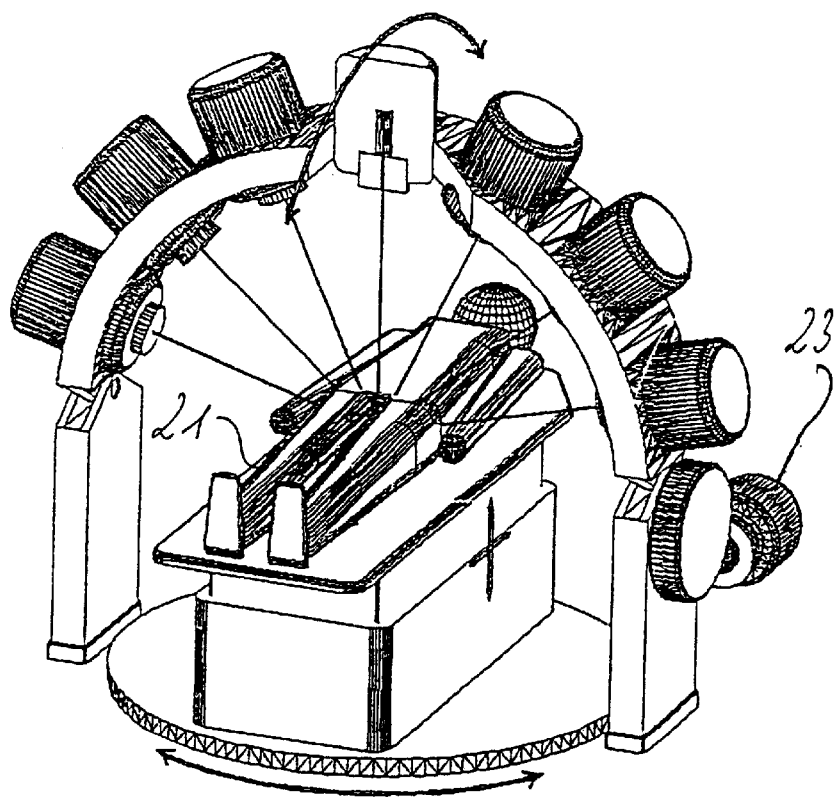

Shown are:

FIG. 1 A three-dimensional representation of a radiation system with a patient resting surface in a first position, and FIG. 2 A three-dimensional representation of a radiation system with a patient resting surface in a second position.

The radiation system in FIG. 1 essentially consists of a gate-shaped radiation part 1 and a table 2 underneath with a patient resting surface 3.

The gate-shaped radiation part 1 has two spaced stands 4 and 5 whose top ends 6, 7 are connected by an arc element 8. The arc element 8 is attached at the top ends 6 and 7 by two bearings 9 and 10. These bearings 9 and 10 allow the arc element 8 to pivot on a line that connects the bearings and forms the pivot axis 11.

Seven essentially semicircular cobalt 60 radiators are in the arc element 8. These radiation sources 12–18 are aimed toward a center 19, and the angle 20 between two neighboring radiation sources 15, 16 is ca 25°.

Each radiation source 12–18 has a diaphragm 21 that is schematically represented in the figure and can be irregularly adjusted.

Under the arc 8, the patient resting surface 3 can be positions so that the intersection 19 of the radiation sources 12–18 lie on a specific point 19 in the body of a person 21 lying on the patient table 3. The patient resting surface 3 is therefore part of the table 2 that allows the patient resting surface to be precisely positioned in space. In addition, the patient resting surface 3 can be rotated on a perpendicular y-axis 22 that intersects the center 19.

When the described radiation system is used, a patient 21 is fist positioned on the patient resting surface 3 so that the connecting axis 11 between the bearings 9 and 10 intersect the body part to be radiated. The bearings 9 and 10 are designed as hollow shafts so that you can look through them to properly position the patient. Alternately, a laser beam can be in the hollow shafts of the bearings 9 and 10 to position the patient.

After the patient is positioned, the radiation sources 12–18 are activated, and the arc element 8 is pivoted slowly on the pivot axis 11 by a drive 23 (FIG. 2). The diaphragms 21 of the radiation sources 12–18 can be in a fixed position, or their position can be changed while the arc element 8 is pivoted. The precise setting of the diaphragms 21 is determined by the shape of the body part to be irradiated. Varying the diaphragm 21 during the pivoting process of the arc element 8 allows optimum radiation that is preferably calculated with a computer.

In addition or alternately to pivoting the arc element 8, the patient resting surface 3 is pivoted on the vertical y-axis 22. This also allows the center 19 to be irradiated from different sides.

While the FIG. 1 describes irradiating a central point 19 in the chest area of a patient 21, FIG. 2 shows a patient 21 being irradiated in the prostate area. The design of the device in FIG. 2 corresponds to the design in FIG. 1.

What is claimed is:

1. A radiation system comprising:
    (a) one or more radiation sources mounted on an arc element and aimed toward a central point, wherein the arc element is arranged to pivot about a first axis;
    (b) a table arranged to rotate on a second axis perpendicular to the first axis.

2. The radiation system of claim 1 wherein the arc element covers an arc of less than about 270°.

3. A The radiation system of claim 1 wherein the arc element covers an arc of about 180°.

4. The radiation system of claim 1 wherein at least one of the first and second axes intersects the central point.

5. The radiation system of claim 1 wherein the first and second axes intersect the central point.

6. The radiation system of claim 1 wherein the arc element comprises a hollow shaft along the first axis.

7. The radiation system of claim 1 wherein each radiation source comprises a diaphragm arranged to control radiation exiting the radiation source.

8. The radiation system of claim 7 wherein each radiation diaphragm is individually adjustable.

9. The radiation system of claim 1 wherein the table can be three dimensionally positioned relative to the arc element.

10. The radiation system of claim 1 comprising from 5 to 10 radiation sources.

11. The radiation system of claim 1 wherein at least one of the one or more radiation sources is moveably mounted on the arc element.

12. The radiation system of claim 1 wherein the radiation sources are positioned at a distance from the center of from about 1 to about 2 m.

13. The radiation system of claim 1 wherein the radiation sources are designed as transportable containers.

\* \* \* \* \*

UNITED STATES PATENT AND TRADEMARK OFFICE
CERTIFICATE OF CORRECTION

PATENT NO. : 6,259,762 B1
DATED : July 10, 2001
INVENTOR(S) : Pastyr et al.

It is certified that error appears in the above-identified patent and that said Letters Patent is hereby corrected as shown below:

<u>Title page, Item [54] and Column 1, line 3,</u>
Title, change "CONTROL" to -- CENTRAL --

Signed and Sealed this

Twelfth Day of November, 2002

Attest:

Attesting Officer

JAMES E. ROGAN
*Director of the United States Patent and Trademark Office*